United States Patent
Bakich et al.

(10) Patent No.: US 6,207,405 B1
(45) Date of Patent: *Mar. 27, 2001

(54) PILOT DRAIN SYSTEM FOR RAPID BIOFILM FORMATION

(75) Inventors: Shannon L. Bakich, Racine; Padma Prabodh Varanasi, Village of Windpoint; Donald M. Milestone, Racine; Mark M. Gipp, Mount Pleasant, all of WI (US)

(73) Assignee: S. C. Johnson & Son, Inc., Racine, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/106,615

(22) Filed: Jun. 29, 1998

(51) Int. Cl.$^7$ ............................... C12Q 1/02; C12M 1/00
(52) U.S. Cl. ....................... 435/29; 435/283.1; 435/289.1
(58) Field of Search .................................. 435/29, 283.1, 435/289.1

(56) References Cited

U.S. PATENT DOCUMENTS 5,928,889 * 7/1999 Bakich et al. ........................ 435/29

OTHER PUBLICATIONS

Effect of Growth Conditions and Substratum Composition on the Persistence of Coliforms in Mixed–Population Biofilms, *Applied & Environmental Microbiology*, Nov. 1996, p. 4014–4018, A. K. Camper, W. L. Jones & J. T. Hayes, Month Not Available.

The Biology of Sphaerotilus Species, *Water Research* Pergamon Press 1968. vol. 2, pp. 597–614, John D. Phaup, Month Not Available.

The Effect of Halogenated Hydantoins on Biofilms, *Corrosion 97*, Paper No. 405 by M. L. Ludyanskiy and F. J. Himpler (NACE International Conference Division, Houston, Texas) (1997), Month Not Available.

Bergey's Manual ® of Systematic Bacteriology, vol. 3; Williams & Wilkins, Baltimore, Maryland (1990), Month Not Available.

The Sphaerotilus–Leptothrix Group of Bacteria, *Microbiological Review*, June 1978 p. 329–356, W. L. van Veen, E. G. Mulder & M. H. Deinema.

Biofilm Formation in the Industry: A Review, *Food Reviews International*, 8(4), 573–603 (1992); Tiina Mattila–Sandholm & Gun Wirtanen, Month Not Available.

Biofilms: Structure and Organisation, *Microbial Ecology in Health and Disease*, vol. 8; 305–308 (1995), J. Wimpenny, Month Not Available.

Microbial Biofilms, *Annu. Rev. Microbial*, 1995, 49: 711–45, J. W. Costerton & Zbigniew Lewandowski; D. E. Caldwell & D. R. Korber; H. M. Lappin–Scott, Month Not Available.

* cited by examiner

Primary Examiner—Louise N. Leary

(57) ABSTRACT

This invention provides a methodology for rapid biofilm formation in a pilot drain system. In a typical embodiment, aqueous nutrient medium and an inoculum comprising both *Sphaerotilus natans* and natural biofilm bacteria is utilized to promote growth of a biofilm mass which occupies at least about 20 percent of the conduit volume of a pilot drain system within a time period of about two weeks under simulated drain usage conditions.

20 Claims, 1 Drawing Sheet

PILOT DRAIN SYSTEM FOR RAPID BIOFILM FORMATION

BACKGROUND OF THE INVENTION

This invention generally relates to methodology for production of experimental biofilm matrices on selected surfaces. More specifically this invention relates to the production of simulated natural biofilms for testing the activities of formulated products for inhibition or removal of the simulated biofilms from a drainage system.

Since 1943 a vast technical literature has developed in connection with advances in biofilm research. The understanding of biofilm processes has progressed rapidly in the last decade. One of the ultimate goals in studying biofilms is to evolve means for manipulating these processes for technological and ecological advantage. Biofilm science is reviewed in publications such as Food Reviews International, 8 (4), 573 (1992), Microbial Ecology in Health and Disease, 8, 305 (1995); Annu. Rev. Microbial, 49, 711 (1995); Applied and Environmental Microbiology, 4014 (November 1996); and "Biofilms" by W. G. Characklis and K. C. Marshall (John Wiley & Sons, Inc., New York, 1989).

As elaborated in the technical literature, a biofilm consists of cells immobilized on a substratum and embedded in an organic polymer matrix of microbial origin. A biofilm is a surface accumulation, which is not necessarily uniform in time or space. A biofilm may be composed of a significant fraction of inorganic or abiotic substances held cohesively by the biotic matrix. A biofilm is a protective matrix for bacteria, with the essential purpose of survival in an environment of limited nutrient supply.

Biofilms consist of both host microbes and their extracellular products, usually exopolysaccharides. Microbes have a tendency to form these protective exopolysaccharide matrices after they have adhered to a surface. The formation of biofilm complexes requires only humid conditions and/or water systems and contact with a support surface and/or interface. With respect to nutrients, a nutrient deficiency in fact may increase the biofilm formation capacity of microbes, as reported in Adv. Appl. Microbiol., 29, 93 (1983).

Biofilms generally can be produced by almost all microbes under suitable conditions. The most common biofilm producers belong to the genera Pseudomonas, Enterobacter, Flavobacterium, Alcaligenes, Staphylococcus, and Bacillus. There also are anaerobes that can construct corrosive biofilms.

Besides causing problems in cleaning and hygiene, biofilms can cause energy losses and blockages in condenser and heat exchange tubes, interfere with water and waste water systems, and form drag-inducing encrustations on ship hulls. In the medical disciplines, a biofilm (referred to as "glycocalyx") formed by bacteria such as a Pseudomonas species can be the systemic causation of diseases of the lungs or the gastrointestinal and urinary tracts. Additionally, a biofilm formed by bacteria such as Staphylococcus species can be a serious contamination problem in foreign-body instruments such as cardiac pacemakers, catheters, prostheses, artificial valves, and the like. Dental plaque is also a typical form of biofilm.

One of the main purposes of natural biofilm formation is for the protection of the host microbes from a hostile environment. As a consequence, there is a combative interaction between microbes in biofilms and biocidal vehicles such as preservatives, disinfectants and antibiotics. Further, the sessile mode of bacterial growth in biofilms differs from that of the same bacteria species that are present as planktonic cells in a circulating aqueous medium which interfaces with the biofilm. Biofilms also act as a trap for nutrient acquisition, which is an important factor when bacteria grow on surfaces and the nutrient supply is oligotrophic.

Because of the manifold ramifications of biofilm formation, there is a serious commitment to biofilm research in a broad range of scientific investigations. Methods of studying biofilm formation include microbiological, physical, and chemical methods. When microbes from extreme natural environments are cultured, standard plate counts usually do not provide accurate estimates. Thus, the classical evaluation methods relying on microbiological plating have questionable value with respect to the laboratory study of biofilms which are intended to achieve authentic correspondence with natural biofilms which exist in the biosphere. In addition, formation of a natural type biofilm in the laboratory environment is difficult, mainly because there are no standardized methodologies currently available.

There is increasing interest in the research and development of methodologies for the production and study of biofilms in a laboratory environment. Accordingly, it is an object of this invention to provide an improved method for the laboratory production of biofilms which simulate natural biofilms that grow under biospheric conditions.

It is another object of this invention to provide a laboratory protocol for simulated natural biofilm production, in combination with a further protocol for testing the activities of formulated products for inhibition or removal of the simulated biofilms as a reliable indicator of the same activities under natural environmental conditions.

Other objects and advantages of the present invention shall become apparent from the accompanying description and examples.

Publications of background interest with respect to the present invention include Water Research Pergamon Press, 2, 597 (1968); Corrosion 97, Paper No. 405 by M. L. Ludyanskiy and F. J. Himpler (NACE Int. Conf. Div., Houston, Tex.); and references cited therein; incorporated herein by reference.

SUMMARY OF THE INVENTION

One or more objects of the present invention are accomplished by the provision of a method for rapid biofilm formation in accordance with a monitored protocol which comprises (1) providing a pilot drain system for liquid flow through a conduit having an average internal diameter between about 0.9–5 centimeters (preferably 0.9–2 centimeters); (2) introducing aqueous nutrient medium and bacterial inoculum comprising sheathed bacteria into the influent end of the conduit to full volume capacity without drainage; (3) maintaining the aqueous suspension medium in the drain conduit for an incubation period sufficient to initiate bacterial attachment to the conduit inner surface; (4) draining the suspension from the effluent end of the drain conduit; (5) recharging and draining the conduit with aqueous nutrient medium at least once every 24 hours of elapsed time period under simulated drain usage conditions to promote biofilm formation on the conduit inner surface; and (6) repeating the aqueous medium recharging and draining cycle of step (5) for an elapsed time period up to about 40 days (preferably up to about 15 days) that is sufficient to yield a biofilm mass which occupies at least about 15 percent of the conduit volume.

Sheathed bacteria genera and species are described in "Bergey's Manual Of Systemic Bacteriology" (Volume 3;

Williams & Wilkins; Baltimore); "Biology Of Microorganisms" (Seventh Edition; Prentice Hall, Englewood Cliffs, N.J.); and Microbiological Reviews, p. 329–356 (June 1978); incorporated by reference.

The Sphaerotilus-Leptothrix group of sheathed bacteria are of particular advantage for purposes of the present invention. Genera species include *Sphaerotilus natans, Leptothrix lopholea, Leplothrix ochracea, Leptothrix cholodnii* and *Leptothrix discophora.*

Figure 1:
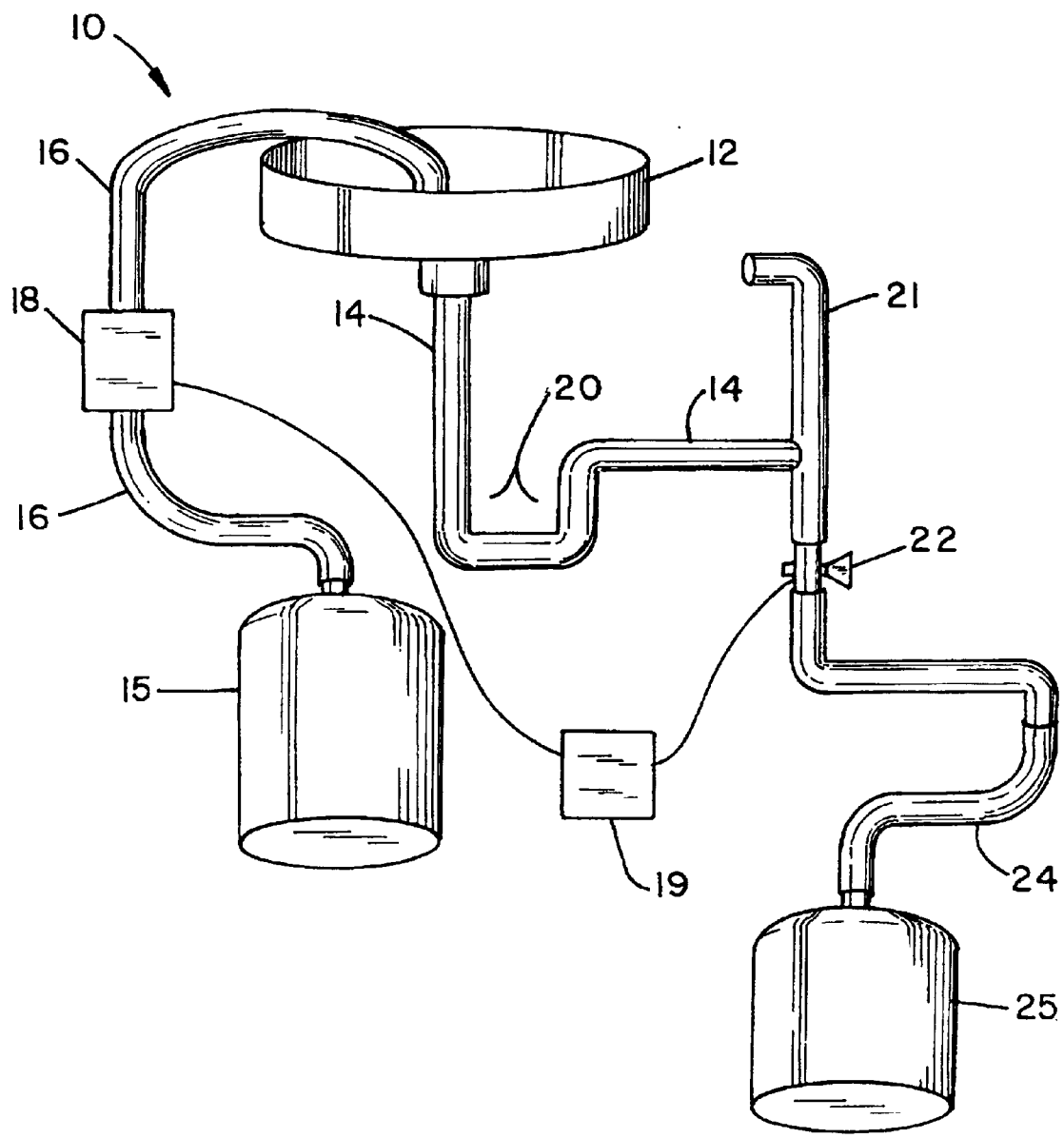
FIG. 1 is an elevational side view of an invention pilot drain system.

As illustrated, pilot drain system 10 comprises sink 12 which is at the influent end of conduit 14. In the drawing, conduit 14 is structured to include P-trap 20, vent pipe 21, and solenoid valve 22. Drainage from conduit 14 flows through line 24 into effluent receptacle 25.

Aqueous nutrient medium is supplied through pump 18 from feed receptacle 15 via line 16 to conduit 14. Timer 19 controls the flow of the aqueous nutrient feed supply, and the drainage of the system through solenoid valve 22.

As illustrated, conduit 14 has a 1.5 centimeter internal diameter, and is constructed of transparent polyvinyl chloride. Conduit 14 can have an internal diameter between about 0.9–5 centimeters, and can be constructed of other materials such as metal or glass.

DESCRIPTION OF SPECIFIC EMBODIMENTS

A standardized nutrient medium can be employed for the biofilm bacterial growth cycles. Suitable nutrient media for biofilm formation are described in technical publications such as Biotechnol. Bioeng., 53 (5), 459 (1997); incorporated herein by reference. A typical nutrient medium contains sources of carbon, nitrogen, phosphate and trace nutrients.

An essential aspect of the present invention pilot drain system is the incorporation of an inoculum comprising Sphaerotilus-Leptothrix type bacteria. *S. Natans* illustrates a preferred species of sheathed bacteria in the present invention. Sheathed bacteria are filamentous organisms with a unique life cycle involving formation of flagellated swarmer cells within a long tube or sheath. Under favorable conditions, vegetative growth occurs within the filament, leading to the formation of long cell-packed sheaths. Under unfavorable conditions, the swarmer cells move out and become dispersed into new environments, leaving behind the empty sheath. Sheathed bacteria are common in freshwater habitats that are rich in organic matter, such as polluted streams, trickling filters, and activated sludge plants, being found primarily in flowing waters,

*S. natans* is a valuable vehicle for purposes of the present invention because of its ability to proliferate rapidly under natural or simulated nutrient conditions. An important feature of a present invention pilot drain system is the rapid formation of a biofilm in a drain conduit for the purpose of testing the activity of a product relative to the simulated biofilm.

During the formation of the biofilm in the pilot drain system, the cycled nutrient medium can include household, business and industrial drain contaminants such as shaving cream, hair, skin cells, grease, paper, foodstuffs, tap water, and the like. In a preferred embodiment, a bacterial inoculum from a natural biofilm is employed together with the *S. natans*. This is illustrated by a bacterial inoculum which is extracted from a household drain biofilm. The monitored protocol in the pilot drain system is designed to provide essential correspondence with simulated household drain conditions, thereby promoting the formation of a simulated biofilm in the reactor which has close correspondence with a household drain natural biofilm.

The term "simulated biofilm" as employed herein refers to a derivative biofilm which has essential phenotypic correspondence with the bacterial consortia of a drain type natural biofilm.

The term "natural biofilm" as employed herein refers to a biospheric surface-mediated bacterial consortium which is in a dynamic relationship with environmental parameters.

The present invention methodology has particular advantage for the preparation of simulated biofilms which are a convenient and reliable vehicle for testing the activities of formulated products, where said products are intended for inhibition or removal of natural biofilms having a phenotypic relationship with the simulated biofilms respectively.

The present invention methodology can be illustrated by reference to a simulated household drain biofilm which is derived from an inoculum comprising *S. natans* and a natural household drain biofilm.

Referring to a pilot drain system as illustrated in FIG. 1, the inoculum and aqueous nutrient medium are introduced into conduit 14, and without drainage the contained liquid volume is recycled through conduit 14 (recycle not shown in FIG. 1) for an incubation period between about 2–48 hours at a temperature between about 15°–45° C.

After the incubation period and drainage of the incubation medium, fresh nutrient medium is recharged and drained in timed cycles to simulate household drain usage conditions. Typically, the nutrient medium recharge and drain cycle is repeated at least once every three hours of elapsed time period.

Within a time period of about 15 days, the simulated biofilm mass inside conduit 14 occupies at least about 20–30 percent of the internal volume of conduit 14.

The methodology of the present invention thus provides a pilot drain system comprising a conduit having an average internal diameter between about 0.9–5 centimeters, and having a biofilm mass on the conduit inner surface which comprises Sphaerotilus-Leptothrix colonies (e.g., *S. natans*) and which occupies at least about 20 percent of the conduit volume. The biofilm preferably contains additional bacterial colonies derived from tap water under simulated household drain usage conditions, and/or bacterial colonies derived from a natural biofilm inoculum.

The pilot drain system methodology of the present invention has general utility for the production of simulated biofilms which are intended for application in a further protocol for testing the activity of an experimental product or a commercial product. The further protocol can include testing the activity of products such as biocides and cleaners, and products for opening conduits which are clogged with biomass, and the like.

The following example is further illustrative of this present invention. The components and specific ingredients are presented as being typical, and various modifications can be derived in view of the fore going disclosure within the scope of the invention.

EXAMPLE

This example illustrates methodology for rapid biofilm growth in a pilot drain system, and the application of the system for testing a drain cleaning product in accordance with the present invention.

A colony of *S. diutans* (ATCC 15291) is streaked onto a CGY plate, and the plate is incubated for 48 hours at 28° C. One colon y from the freshly-grown plate is inoculated into 100 mL of CGY medium and incubated overnight in a shaking incubator.

The CGY medium has the following composition:

| | |
|---|---|
| Casitone (Difco 0259) | 5 g |
| Glycerol | 10 g |
| Yeast Autolysate | 1 g |
| Distilled water | 1 L |

A pilot drain system corresponding to FIG. 1 is employed, with accessory equipment not illustrated in FIG. 1. The drain system is filled with 115 mL of CGY medium, and the medium is inoculated with 10 mL of the *S. natans* preparation. Recycle tubing is used to circulate 125mL of the drain system liquid medium for 24 hours. After 24 hours, the CGY medium is drained, and timed recharge and draining of medium in the pilot drain system is commenced. CGY medium is charged to the drain system conduit, and after 40 seconds the medium is drained. This cycle is repeated once every hour for 10 hours a day, over a lapsed time period of about 10–20 days until there is about a 30 percent reduction in the free volume of the drain conduit.

Optionally, the inoculum includes authentic natural drain biofilm bacteria, and the nutrient medium includes shaving cream, hair, skin cells or other household drain contaminants of specific concern.

Volume Measurement

A rubber stopper is used to plug the effluent end of the drain system. Deionized water (200 grams) is poured into the influent conduit until the water level fills the lateral section and reaches the vent pipe. The weight of the added water is determined, and this is converted into a volume value (a density of 1 g/mL).

The rubber stopper is removed, and the water content is drained. Three volume measurements are conducted and the results are averaged.

When the biofilm begins to form, the volume measurements are conducted once every 2–3 days. Flow rate measurement is not commenced until there is at least a 30 percent reduction in the measured volume.

Flow Rate Measurement

A rubber stopper is used to plug the effluent end of the drain system. Deionized water (1500 mL) is poured into the sink section. The plug is removed, and the time for sink drainage is recorded.

The flow rate is measured once a day, and the measurement is repeated five times to calculate a statistical average.

Treatment Of Biofilm In Pilot Drain System

For testing the activity of a cleaning product, at least two identical pilot drain systems are operated simultaneously to grow biofilm in the respective drain conduits.

A sample of a cleaning product (Liquid DRANO®, 4 ounces) is charged to one drain system, and an equal volume of deionized water is charged to a comparable drain system.

The treatments are held in the conduits for 15 minutes. The treatments then are drained, and the conduits are rinsed with a gallon of warm water (45° C.). Flow rate and volume measurements are conducted immediately to determine the effect of the cleaner activity on the pilot drain system biofilm mass. The measurements are repeated about 24 hours after treatment.

If regrowth of the biofilm is to be determined, the nutrient feed procedure is resumed, and the respective protocols are conducted.

What is claimed is:

1. A method for rapid biofilm formation in accordance with a monitored protocol which comprises (1) providing a pilot drain system for liquid flow through a conduit having an average internal diameter between about 0.9–5 centimeters; (2) introducing aqueous nutrient medium and bacterial inoculum comprising sheathed bacteria into the influent end of the conduit to full volume capacity without drainage; (3) maintaining the aqueous suspension medium in the drain conduit for an incubation period sufficient to initiate bacterial attachment to the conduit inner surface; (4) draining the suspension from the effluent end of the drain conduit; (5) recharging and draining the conduit with aqueous nutrient medium at least once every 24 hours of elapsed time period under simulated drain usage conditions to promote biofilm formation on the conduit inner surface; and (6) repeating the recharging and draining cycle of step (5) for an elapsed time period up to about 40 days that is sufficient to yield a biofilm mass which occupies at least about 20 percent of the conduit volume.

2. The method in accordance with claim 1 wherein the pilot drain system conduit includes a P-trap structure.

3. The method in accordance with claim 1 wherein the pilot drain system conduit is transparent.

4. The method in accordance with claim 1 wherein the inoculum includes bacteria derived from a natural biofilm.

5. The method in accordance with claim 1 wherein the sheathed bacteria inoculum in step (2) comprises Sphaerotilus-Leptothrix species.

6. The method in accordance with claim 1 wherein the sheathed bacteria inoculum in step (2) comprises *Sphaerotilus natans*.

7. The method in accordance with claim 1 wherein the aqueous nutrient medium in step (2) comprises casitone, glycerol and yeast autolysate ingredients.

8. The method in accordance with claim 1 wherein the incubation period in step (3) is between about 2–48 hours at a temperature between about 15°–45° C.

9. The method in accordance with claim 1 wherein the aqueous nutrient medium recharging and draining cycle in step (5) is repeated at least once every 3 hours of elapsed time period.

10. The method in accordance with claim 1 wherein the aqueous nutrient medium in step (5) contains waste contaminants having correspondence with simulated drain usage.

11. The method in accordance with claim 1 wherein the biofilm mass in step (6) comprises Sphaerotilus-Leptothrix and natural biofilm bacterial colonies derived under simulated drain usage conditions.

12. The method in accordance with claim 1 wherein the biofilm mass in step (6) occupies at least about 30 percent of the conduit volume.

13. The method in accordance with claim 1 wherein the pilot drain system and its biofilm mass content is utilized in a further protocol for testing the activity of a product.

14. The method in accordance with claim 1 wherein the pilot drain system and its biofilm mass is utilized in a further protocol for testing the activity of a cleaning product, or a cleaning device.

15. The method in accordance with claim 1 wherein the pilot drain system and its biofilm mass is utilized in a further protocol for testing the activity of a product for opening conduits which are clogged with biomass.

16. A pilot drain system and its biofilm mass as provided in accordance with the method of claim 1.

17. A pilot drain system comprising a conduit having an average internal diameter between about 0.9–5 centimeters, and having a biofilm mass on the conduit inner surface which comprises Sphaerotilus-Leptothrix colonies and which occupies at least about 20 percent of the conduit volume.

18. The pilot drain system in accordance with claim 17 wherein the biofilm mass comprises Sphaerotilus-Leptothrix and natural biofilm bacterial colonies derived under simulated household drain usage conditions.

19. The pilot drain system in accordance with claim 17 wherein the biofilm mass comprises Sphaerotilus-Leptothrix and bacterial colonies derived from a natural biofilm inoculum.

20. A pilot drain system comprising a conduit having an average internal diameter between about 0.9–5 centimeters, and having a biofilm mass on the conduit inner surface which comprises *Sphaerotilus natans* colonies and which occupies at least about 20 percent of the conduit volume.

* * * * *